United States Patent [19]
Vacca et al.

[11] Patent Number: 5,629,324
[45] Date of Patent: May 13, 1997

[54] THROMBIN INHIBITORS

[75] Inventors: Joseph P. Vacca, Telford; William C. Lumma, Pennsburg; Stephen F. Brady, Philadelphia; Thomas J. Tucker, North Wales, all of Pa.

[73] Assignee: Merck & Co., Inc., Rahway, N.J.

[21] Appl. No.: 419,683

[22] Filed: Apr. 10, 1995

[51] Int. Cl.$^6$ .................. A61K 31/445; C07D 401/06
[52] U.S. Cl. .................. 514/316; 514/318; 514/320; 514/325; 514/326; 546/189; 546/193; 546/196; 546/203; 546/208
[58] Field of Search .................. 546/193, 196, 546/203, 208, 189; 514/318, 320, 325, 326, 316

[56] References Cited

U.S. PATENT DOCUMENTS

| | | | |
|---|---|---|---|
| 5,252,566 | 10/1993 | Shuman | 514/210 |
| 5,332,726 | 7/1994 | Klein | 514/18 |
| 5,380,713 | 1/1995 | Balasubramanian | 514/18 |
| 5,416,093 | 5/1995 | Shuman | 514/307 |

FOREIGN PATENT DOCUMENTS

| | | |
|---|---|---|
| 52881/86 | 1/1986 | Australia . |
| 0363284A2 | 4/1990 | European Pat. Off. . |
| 0471651A2 | 2/1992 | European Pat. Off. . |
| 0479489A2 | 4/1992 | European Pat. Off. . |
| 603112A1 | 6/1994 | European Pat. Off. . |
| 601459A2 | 6/1994 | European Pat. Off. . |
| 0648780A1 | 8/1994 | European Pat. Off. . |
| 648780 | 4/1995 | European Pat. Off. . |
| 92/14750 | 3/1992 | WIPO . |
| WO92/07869 | 5/1992 | WIPO . |
| 94/29336 | 12/1994 | WIPO . |

OTHER PUBLICATIONS

Bajusa et al. "Highly active and selective atcoagulants:D-phe-pro-arg-H, a free tripeptide adehyde..." J. Med. Che. v. 33, pp. 1729–1735 (1990).
Banner et al. "Serine proteases: 3D structure, mechanism of action and inhibitors" Persp. Med. Chem. Testa Bernard Ed. Verlag (pubsh.) pp. 29–43 (1993).
Balasubramanian, et al. J. Med. Chem. 1993, 36, No. 2 pp. 300–303.
Shuman et al. J. Med. Chem., 1993, 36, No. 3 pp. 314–319.
Kettner et al. The Journal of Biol. Chem., vol. 265, No. 30, Issue of Oct. 25; pp. 18289–18297 1990.
J. Biol. Chemistry, Platelet Glycocalicin vol. 263, No. 10, pp. 3435–3443, T. Okumura et al. (1978).
J. of Biol. Chem., The Binding of Thrombin to the Surface of Human Platelets, vol. 249, No. 8 pp. 2646–2651, 1974, Tollefsen et al.
Cell., Molecular Cloning of a Functional Thrombin..., vol. 64, pp. 1057–1068, Mar. 22, 1991.
J. of Biol. Chemistry, Thrombin Interaction with Platelets, vol. 262, No. 7 pp. 3030–3036 (1987), Gronke et al.
J. of Biol. Chem., Structure–Function Relations in the Interaction of alpha–Thrombin wth Blood Platelets, vol. 252, No. 20, 7118–7123 (1977), Workman et al.

Biochemical & Biophysical Research Commun., Minimal Sequence Requirement of Thrombin Receptor Agonist Peptide, vol. 184, No. 2 pp. 790–796 (1992), Kwan Y. Hui et al.
J. of Biol. Chem., Communication, vol. 267, No. 19, Jul., pp. 13146–13149, Scarborough et al. (1992).
J. of Biol. Chem., "Structure–Function Relationships in the Activation of Platelet Thrombin Receptors by Receptor-derived Peptides", vol. 267, No. 9, pp. 6081–6085, 1992, Vassallo et al. (1992).
Organic & Medicinal Chemistry Letters, alpha–Hydroxy–and alpha–Ketoester Functionalized Thrombin Inhibitors, vol. 2, No. 12, pp. 1607–1612, Iwanowicz et al., (1992).
J. Am. Chem. Soc., Design, Synthesis and Kinetic Evaluation of a Unique Cladd of Elastase Inhibitors..., 114, 1854–1863, Edwards et al. (1992).
Thrombos, Diathes, haemorrh. (Stuttg.), Thrombin Interaction with Human Platelets... 1974, 32, 207, David R. Phillips.
Chapter 3, Dept. of Biochemistry, St. Jude Children's Research Hospital, Platelet membrane proteins:composition and receptor function, Berndt and Phillips (1981).
Biochemistry, Platelet Stimulation by Thrombin and Other Proteases, vol. 14, No. 6, 1975, Martin et al.
Blood, PPack–Thrombin Inhibits Thrombin–Induced Platelet Aggregation... vol.75, No. 10 1990, pp. 1983–1990, Greco et al.
The Embo Journal, The refined 1.9 A crystal structure of human alpha–thrombin..., vol. 8, No. 11 pp. 3467–3475, Bode et al. (1989).
Elsevier Science Publishers Ltd. vol. 14, Oct. 1993, Tappanelli et al.
Piptides, vol. 12, pp. 1153–1154, Anticoagulant Activity of a Peptide Boronic Hussain et al. (1991).

*Primary Examiner*—Ceila Chang
*Attorney, Agent, or Firm*—Richard S. Parr; Melvin Winokur

[57] ABSTRACT

Compounds of the invention have the following structure:

for example

These compounds inhibit thrombin and associated thrombosis.

9 Claims, No Drawings

THROMBIN INHIBITORS

BACKGROUND OF THE INVENTION

Thrombin is a serine protease present in blood plasma in the form of a precursor, prothrombin. Thrombin plays a central role in the mechanism of blood coagulation by convening the solution plasma protein, fibrinogen, into insoluble fibrin.

Edwards et al. *J. Amer. Chem. Soc.* (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

Thrombin inhibitors described in prior publications contain sidechains of arginine and lysine. These structures show low selectivity for thrombin over other trypsin-like enzymes. Some of them show toxicity of hypotension and liver toxicity.

European Publication 601 459 describes sulfonamido heterocyclic thrombin inhibitors, such as N-[4-[(aminoiminomethyl)amino]butyl]-1-[N-(2-naphthalenylsulfonyl)-L-phenylalanyl]-L-prolinamide.

WO 94/29336 describes compounds which are useful as thrombin inhibitors.

SUMMARY OF THE INVENTION

Compounds of the invention have the following structure:

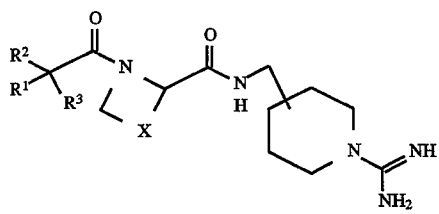

wherein $R_1$ and $R_2$ are independently
hydrogen,
phenyl unsubstituted, mono- or di-substituted with OH, $C_{1-4}$ alkyl, oxo, or halo,
naphthyl,
biphenyl,
a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
$C_{1-4}$ alkyl,
branched $C_{1-4}$ alkyl,
$C_{3-7}$ cycloalkyl,
$C_{5-12}$ bicyclic alkyl,
$C_{11-16}$ tricyclic alkyl,
$R^4(CH_2)_n$;
$(R^4)_2CH$, wherein $R^4$ is the same or different,
$(R^4)(R^4O)CH$, wherein $R^4$ is the same or different,
$R^4O(CH_2)_n$, or
$R^2$ may be joined with $R^1$ to form a four- to seven membered carbon ring in which zero to two carbon atoms may be substituted with heteroatoms independently selected from the list N, O, and S,
where n is 1, 2, 3 or 4;
$R^3$ is
H,
$HO(CH_2)_p$, where p is 0, 1, 2, 3 or 4;
$R^4$ is
phenyl unsubstituted, mono- or di-substituted with OH, OMe, $C_{1-4}$ alkyl, oxo, or halo,
naphthyl,
biphenyl,
a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
$C_{1-4}$ alkyl,
branched $C_{1-4}$ alkyl,
$C_{3-7}$ cycloalkyl,
$C_{5-12}$ bicyclic alkyl, or
$C_{11-16}$ tricyclic alkyl; and
X is
$(CH_2)q$ where q is 1 or 2,
$NR^1CH_2$, or
$SCH_2$.

These compounds show selectivity for thrombin inhibition over inhibition of trypsin and other trypsin-like enzymes and have oral bioavailability. Trypsin-like enzymes (such as trypsin, thrombin, factor xa, kallikrein, plasmin, urokinase, and plasminogen activator) are serine dependent enzymes that catalyze hydrolysis at arginyl and lysyl peptide bonds.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carder. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION

Compounds of the invention have the following structure:

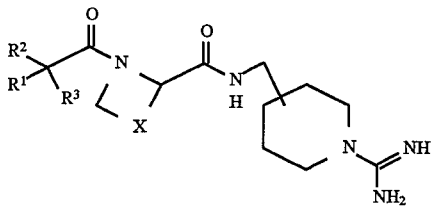

wherein $R^1$ and $R^2$ are independently
  hydrogen,
  phenyl unsubstituted, mono- or di-substituted with OH, $C_{1-4}$ alkyl, oxo, or halo,
  naphthyl,
  biphenyl,
  a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
  $C_{1-4}$ alkyl,
  branched $C_{1-4}$ alkyl,
  $C_{3-7}$ cycloalkyl,
  $C_{5-12}$ bicyclic alkyl,
  $C_{11-16}$ tricyclic alkyl,
  $R^4(CH_2)_n$,
  $(R^4)_2CH$, wherein $R^4$ is the same or different,
  $(R^4)(R^4O)CH$, wherein $R^4$ is the same or different,
  $R^4O(CH_2)_n$, or
  $R^2$ may be joined with $R^1$ to form a four- to seven membered carbon ring in which zero to two carbon atoms may be substituted with heteroatoms independently selected from the list N, O, and S,
where n is 1, 2, 3 or 4;
$R^3$ is
  H,
  $HO(CH_2)_p$, where p is 0, 1, 2, 3 or 4;
$R^4$ is
  phenyl unsubstituted, mono- or di-substituted with OH, OMe, $C_{1-4}$ alkyl, oxo, or halo,
  naphthyl,
  biphenyl,
  1-dibenzocycloheptene,
  a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
  $C_{1-4}$ alkyl,
  branched $C_{1-4}$ alkyl,
  $C_{3-7}$ cycloalkyl,
  $C_{5-12}$ bicyclic alkyl, or
  $C_{11-16}$ tricyclic alkyl; and
X is
  $(CH_2)q$ where q is 1 or 2,
  $NR^1CH_2$, or
  $SCH_2$.

In one class of compounds of the invention, the compounds have the structure

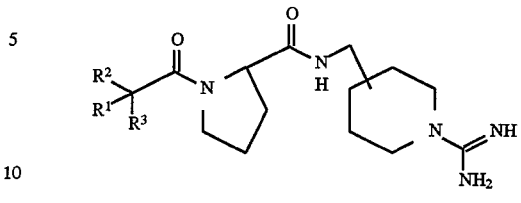

wherein $R^1$ and $R^2$ are independently
  hydrogen,
  phenyl unsubstituted, mono- or di-substituted with OH, $C_{1-4}$ alkyl, oxo, or halo,
  naphthyl,
  biphenyl,
  a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
  $C_{1-4}$ alkyl,
  branched $C_{1-4}$ alkyl,
  $C_{3-7}$ cycloalkyl,
  $C_{5-12}$ bicyclic alkyl,
  $C_{11-16}$ tricyclic alkyl,
  $R^4(CH_2)_n$,
  $(R^4)_2CH$, wherein $R^4$ is the same or different,
  $(R^4)(R^4O)CH$, wherein $R^4$ is the same or different,
  $R^4O(CH_2)_n$, or
  $R^2$ may be joined with $R^1$ to form a four- to seven membered carbon ring in which zero to two carbon atoms may be substituted with heteroatoms independently selected from the list N, O, and S,
where n is 1, 2, 3 or 4;
$R^3$ is
  H,
  $HO(CH_2)_p$, where p is 0, 1, 2, 3 or 4; and
$R^4$ is
  phenyl unsubstituted, mono- or di-substituted with OH, OMe, $C_{1-4}$ alkyl, oxo, or halo,
  naphthyl,
  biphenyl,
  1-dibenzocycloheptene,
  a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
  $C_{1-4}$ alkyl,
  branched $C_{1-4}$ alkyl,
  $C_{3-7}$ cycloalkyl,
  $C_{5-12}$ bicyclic alkyl, or
  $C_{11-16}$ tricyclic alkyl.

In a subclass of this class of compounds of the invention, the compounds have the structure

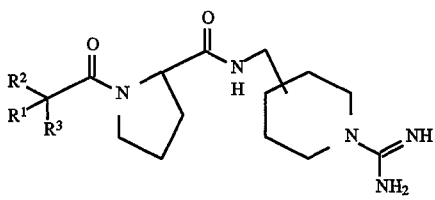

wherein $R^1$ and $R^2$ are independently hydrogen, phenyl unsubstituted, mono- or di-substituted with OH, $C_{1-4}$ alkyl, oxo, or halo, $(R^4)_2CH$, wherein $R^4$ is the same or different, $R^2$ may be joined with $R^1$ to form a four- to seven membered carbon ring in which zero to two carbon atoms may be substituted with heteroatoms independently selected from the list N, O, and S, where n is 1, 2, 3 or 4;

$R^3$ is

H, $HO(CH_2)_p$, where p is 0, 1, 2, 3 or 4; and $R^4$ is phenyl unsubstituted, mono- or di-substituted with OH, OMe, $C_{1-4}$ alkyl, oxo, or halo, 1-dibenzocycloheptene, or a 6-membered monocyclic heterocyclic ring which may be saturated or unsaturated, and which consists of carbon atoms and from one to three N heteroatoms, $C_{3-7}$ cycloalkyl.

Specific embodiments of this subclass include

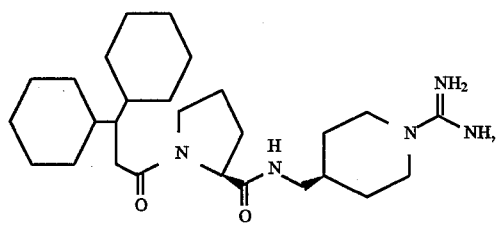

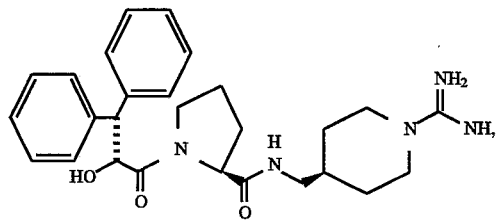

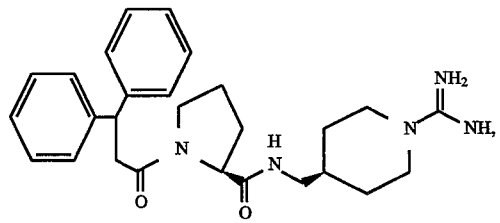

-continued

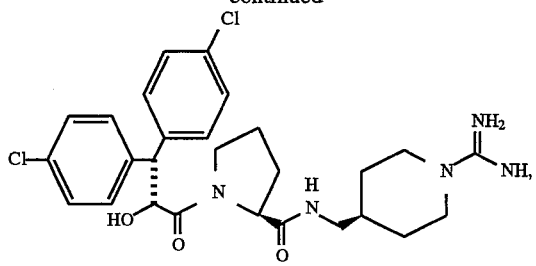

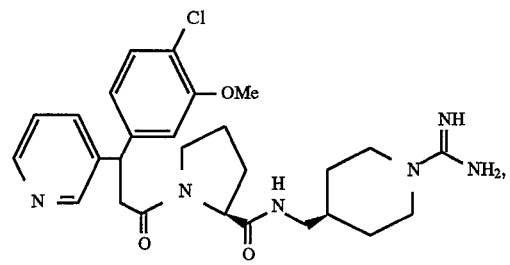

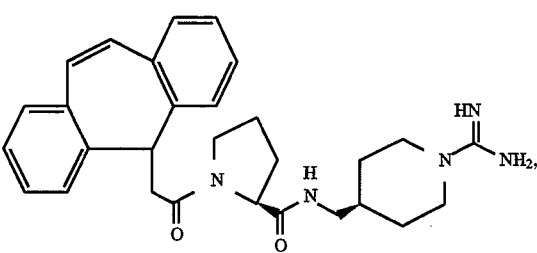

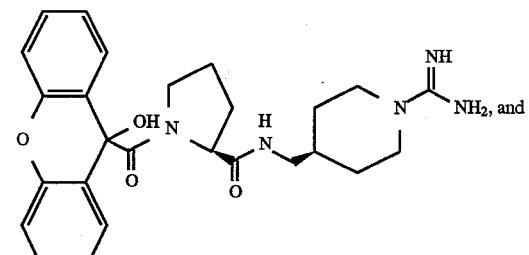

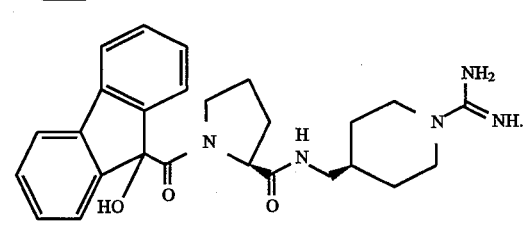

Another embodiment of the invention is

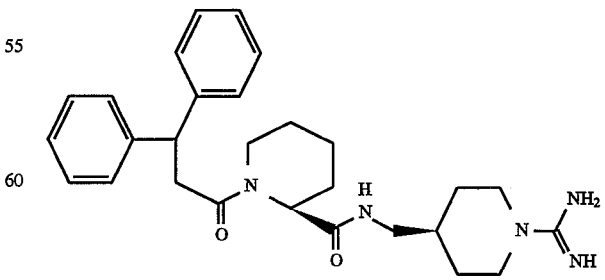

Some abbreviations that may appear in this application are as follows.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT(HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride |
| | Other |
| (BOC)₂O (BOC₂O) | di-t-butyl dicarbonate |
| n-Bu₄N+F− | tetrabutyl ammonium fluoride |
| nBuLi (n-Buli) | n-butyllithium |
| DMF | dimethylformamide |
| Et₃N | triethylamine |
| EtOAc | ethyl acetate |
| TFA | trifluoroacetic acid |
| DMAP | dimethylaminopyridine |
| DME | dimethoxyethane |
| LDA | lithium diisopropylamide |
| THF | tetrahydrofuran |
| | Amino Acid |
| Ile | Isoleucine |
| Phe | Phenylalanine |
| Pro | Proline |
| Ala | Alanine |
| Val | Valine |

The compounds of the present invention may have chiral centers and occur as racemates, racemic mixtures and as individual diastereomers, or enantiomers with all isomeric forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluroacetate, perchlorate, nitrate, benzoate, maleate, tartrate, hemitartrate, benzene sulfonate, and the like.

The term heterocycle or heterocyclic, as used herein except where noted, represents a stable 5-to 7-membered mono- or bicyclic or stable 7-to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Amide couplings used to form the compounds of this invention are typically performed by the carbodiimide method with reagents such as dicyclohexylcarbodiimide, or 1-ethyl-3-(3-dimethyl-aminopropyl) carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

The compounds shown in the tables below are exemplary compounds of the present invention:

TABLE 2

| G | Ki (nM vs thrombin) |
|---|---|
| (diphenylmethyl) | 2.7 |
| (9-hydroxyfluorenyl) | 1.1 |

The following synthetic routes can be used to prepare compounds of the invention. Using method I 4-aminomethyl-BOC-piperidine is coupled to CBZ-L-proline using standard amide coupling procedures. The CBZ group is then removed via hydrogenation and the proline amine is coupled with an acid such as 9-hydroxy-flourene-carboxylic acid. The BOC group is removed from the piperidine, and the amine is converted to the guanidine using a guanylating reagent such as amidinosulfonic acid.

METHOD 1

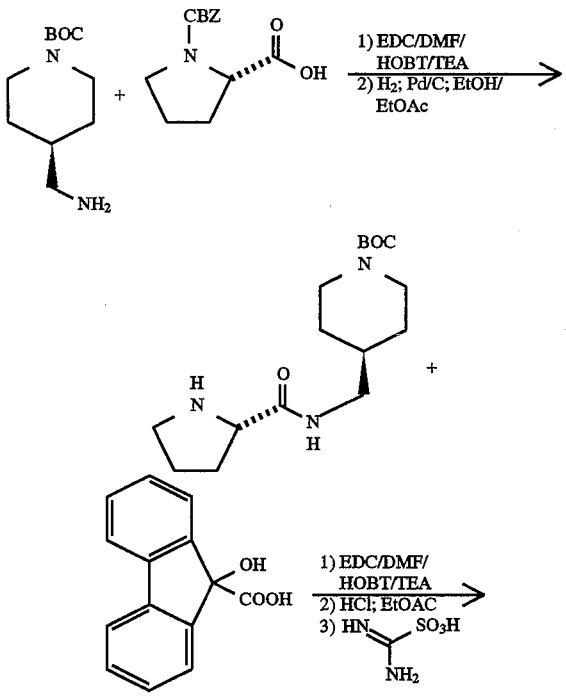

-continued
METHOD 1

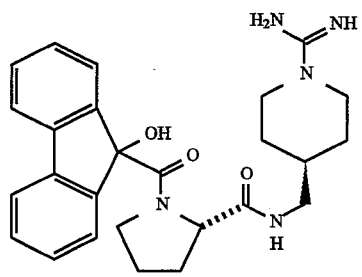

A second method for constructing the compounds of general structure I (as exemplified by examples 1 and 2) is to react an acid such as 9-hydroxy-flourene-carboxylic acid or 3,3-diphenyl-propionic acid with L-proline-methyl ester. The ester group is hydrolyzed and the acid is then coupled with 4-aminomethyl-Boc-Piperidine. The BOC group is removed with an acid such as HCl or trifluoroacetic acid, and the resultant amine is reacted with amidine-sulfonic acid to afford the desired product.

METHOD 2

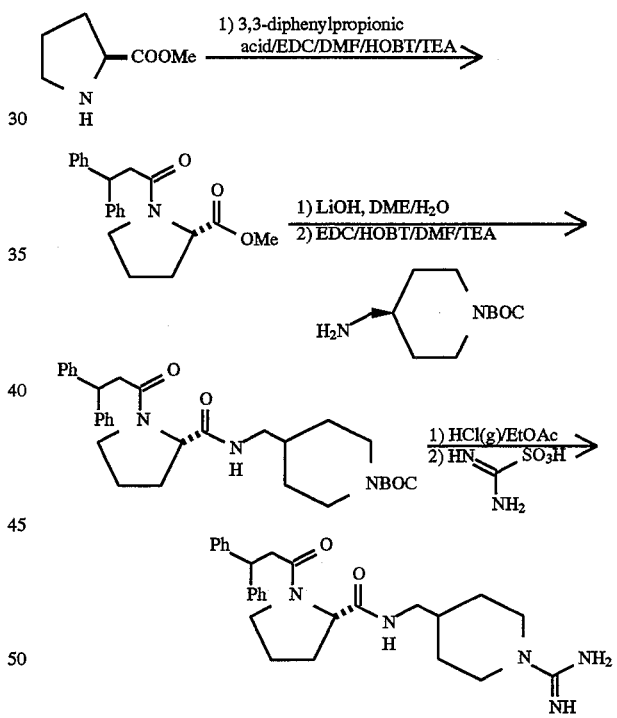

EXAMPLE 1

Preparation of
N'-[[1-(Aminoiminomethyl)-4-piperidinyl]methyl]-
N-(3,3-diphenylpropinyl)-L-proline Amide Step A: N-(3,3-diphenylpropionyl-L-proline methylester To a solution of 3,3 Diphenylpropionic acid (2.00 g, 8.85 mmol) in DMF (20 mL) was added EDC (2.04 g, 10.62 mmol), HOBT (1.44 g, 10.62 mmol) and L-proline methyl ester hydrochloride (1.76 g, 10.62 mmol) with stirring at ambient temperature. Triethylamine (2.96 mL, 21.24 mmol) was added to adjust the pH of the mixture to 8.5. After 24 hrs the DMF was removed under reduced pressure and the residue was partitioned between EtOAc (100 mL)- H₂O (50 mL). The aqueous layer was washed with EtOAc (2×50 mL), organics combined, washed with 10% citric acid soln, aq satd NaHCO₃ soln, brine and dried (Na₂SO₄). Filtration and concentration to dryness gave 3.50 g of crude product which was chromatographed (SiO₂)eluting with 99 CH₂Cl₂:1 MeOH to 98 CH₂Cl₂:2 MeOH to give 2.48 g (83%) of N-(3,3-diphenylpropionyl)-L-proline methylester.

Step B: N-(3,3-diphenylpropionyl)-L-proline

N-(3,3-diphenylpropionyl)-L-proline methylester (2.10 g, 6.23 mmol) was dissolved in DME (50 ml) and H₂O (50 ml). Lithium hydroxide monohydrate (1.57 g, 37.39 mmol) was added and the mixture was stirred at ambient temperature for 2 hrs. The reaction mixture was concentrated to remove DME and the remaining aqueous layer was acidified with 1N HCl to pH 3. The acidic layer was washed with EtOAc (3×75 ml). Organic washes were combined, dried with Na₂SO₄, filtered and concentrated to give 1.92 g (94%) of N-(3,3-diphenylpropionyl)-L-proline.

Step C: N'-[[1-(t-Butyloxycarbonyl)-4-piperidinyl]methyl]-N-(3,3-diphenylpropionyl-L-proline amide To a solution of N-(3,3-diphenylpropionyl)-L-proline (0.600 g, 1.83 mmol) in DMF (8 mL) was added EDC (0.422 g, 2.20 mmol), HOBT (0.297 g, 2.20 mmol) and N-1-(t-butyloxycarbonyl) aminomethyl piperidine (0.471 g, 2.20 mmol) with stirring at ambient temperature. Triethylamine (0.307 mL, 2.20 mmol) was added to adjust the pH of the mixture to 8.5. After 24 hrs the DMF was removed under reduced pressure and the residue was partitioned between EtOAc (50 mL)-H₂O (25 mL). The aqueous layer was washed with EtOAc (2×25 mL), organics combined, washed with aq satd NaHCO₃ soln, brine and dried (Na₂SO₄). Filtration and concentration to dryness gave 0.960 g of crude product which was chromatographed (SiO₂) eluting with 99 CH₂Cl₂:1 MeOH to 98 CH₂Cl₂:2 MeOH to give 0.750 g (79%) of N'-[[1-(t-Butyloxycarbonyl)-4-piperidinyl]methyl]-N-(3,3-diphenylpropionyl)-L-proline amide.

Step D: N'-[4-piperidinylmethyl]-N-(3,3-diphenylpropionyl)-L-proline amide hydrochloride HCl gas was bubbled into a soln of N'-[[1-(t-Butyloxycarbonyl)-4-piperidinyl]methyl]-N-(3,3-diphenylpropionyl)-L-proline amide (0.750 g, 1.45 mmol) in EtOAc (75 mL) at −20° C. for 5 min. The mixture was capped and allowed to stir at ambient temperature for 1 hr. The solution was concentrated to dryness to give 0.656 g (100%) of N'-[4-piperidinylmethyl]-N-(3,3-diphenylpropionyl)-L-proline amide hydrochloride which was used without further purification.

Step E: N'-[[1-(Aminoiminomethyl)-4-piperidinyl]methyl]-N-(3,3-diphenylpropionyl)-L-proline amide N'-[4-piperidinylmethyl]-N-(3,3-diphenylpropionyl)-L-proline amide hydrochloride (0.650 g, 0.1.43 mmol) was dissolved in DMF (6 mL) and treated with triethylamine (0.438 ml, 3.15 mmol) and amidine sulfonic acid (0.195 g, 1.57 mmol) with stirring at ambient temperature. After stirring for 72 hrs and removal of the DMF, the residue was purified by prep. HPLC. Pure fractions were combined and lyopholized to give 440 mg of N'-[[1-(Aminoiminomethyl)-4-piperidinyl]methyl]-N-(3,3-diphenylpropionyl)-L-proline amide

EXAMPLE 2

Preparation of
N'-[[1-(Aminoiminomethyl)-4-piperidinyl]methyl]-N-(9-hydroxyfluorene-9-carboxy)-L-proline Amide Step A: N-(9-hydroxyfluorene-9-carboxyl)-L-proline methylester To a solution of L-proline methyl ester hydrochloride (0,225 g, 1.36 mmol) in dimethylacetamide (DMA, 15 mL) was added EDC (0.366 g, 1.91 mmol), HOBT (0.251 g, 1.64 mmol) and 9-hydroxyfluorene-9-carboxylic acid (0.371 g, 1.64 mmol) with stirring at ambient temperature. N-methylmorpholine was added to adjust the pH of the mixture to 7.5–8. After 5 days the DMA was removed under reduced pressure and the residue was partitioned between EtOAc (100 mL)- H₂O (50 mL). The aqueous layer was washed with EtOAc (2×50 mL), organics combined, washed with 10% KHSO4soln, 2× water, 1× aq satd NaHCO₃ soln, 2× brine and dried (Na₂SO₄). Filtration and concentration to dryness gave 0.538 g of crude product which was used as is in the next reaction.

Step B: N-(9-hydroxyfluorene-9-carboxyl)-L-proline

N-(9-hydroxyfluorene-9-carboxyl)-L-proline methylester (0.539 g, 1.6 mmol) was dissolved in 20 ml of 50% THF and H₂O. 1.0 ml (2 mmol) of a 2N Lithium hydroxide solution was added and the mixture was stirred at ambient temperature for 4.5 hrs. The reaction mixture was followed to completion via TLC (12:2:2:10; EtOAc:HOAc:IsoOct:H2o). The mixture was then adjusted to pH<2 with KHSO₄ solution and partitioned between EtOAc (100 mL) and H₂O (50 mL). The aqueous layer was removed and the EtOAc washed 2× with brine, 1× H₂O, dried over Na₂SO₄, filtered and concentrated to afford 400 mg of (90%) of N-(9-hydroxyfluorene-9-carboxyl)-L-proline.

Step C: N'-[[1-(t-Butyloxycarbonyl)-4-piperidinyl]methyl]-N-(9-hydroxyfluorene-9-carboxyl)-L-proline amide To a solution of N-1-(t-butyloxycarbonyl) aminomethyl piperidine (0.308 g, 1.44 mmol) in DMF (15 mL) was added EDC (0.395 g, 2.06 mmol), HOBT (0.265 g, 1.73 mmol) and N-(9-hydroxyfluorene-9-carboxyl)-L-proline (0.557 g, 1.72 mmol) with stirring at ambient temperature. N-methylmorpholine was added to adjust the pH of the mixture to 7.5–8. After 5 days an additional amount of N-(9-hydroxyfluorene-9-carboxyl)-L-proline (1.15 mmol), HOBT (0.32 mmol) and EDC (1.44 mmol) was added to the reaction. After an additional 24 hrs, the DMF was removed under reduced pressure and the residue was partitioned between EtOAc (100 mL)- H₂O (75 mL). The aqueous layer was washed with EtOAc (2×50 mL), organics combined, washed with 10% KHSO₄ solution, 2× H2O, 1× 10% NaHCO3 solution, 1× brine and dried over Na₂SO₄. Filtration and concentration to dryness gave 1.068 g of crude product which was 49% pure by reverse phase HPLC.

Step D: N'-[4-piperidinylmethyl]-N-(9-hydroxyfluorene-9-carboxyl)-L-proline amide trifluoroacetate 1.068 g of crude N'-[[1-(t-Butyloxycarbonyl)-4-piperidinyl]methyl]-N-(9-hydroxyfluorene-9-carboxyl)-L-proline amide was dissolved in 40 ml of 50% trifluoroacetic acid/50% methylene chloride and mixed at room temperature for 25 minutes. The TFA/CH₂Cl₂ was removed under reduced pressure and the residue yielded 1.07 g of crude product which was 40% pure via HPLC. This was used in the next step without further purification.

Step E: N'-[[1-(Aminoiminomethyl)-4-piperidinyl]methyl]-N-(9-hydroxyfluorene-9-carboxyl)-L-proline amide N'-[4-piperidinylmethyl]-N-(9-hydroxyfluorene-9-carboxyl)-L-proline amide trifluoroacetate (1.07 g) was dissolved in DMF (20 mL) and treated with triethylamine (0.440 ml, 3.54 mmol) and amidine sulfonic acid (0.199 g, 1.61 mmol) with stirring at ambient temperature. After two days, an additional amount of amidine sulfonic acid (0.184 g, 1.48 mmol) and triethylamine (0.205 mL, 1.48 mmol) was added. After stirring for a total of four days, the DMF was removed and the residue was purified by prep. HPLC. Pure fractions were combined and lyopholized to give 114 mgs of N'-[[1-(Aminoiminomethyl)-4-piperidinyl]methyl]-N-(9-hydroxyfluorene-9-carboxyl)-L-proline amide trifluoroacetate.

In Vitro Assay For Determining Proteinase Inhibition

Assays of human a-thrombin and bovine trypsin were performed at 25° C. in 0.05M TRIS buffer pH 7.4, 0.15M NaCl, 0.1% PEG. Trypsin assays also contained 1 mM $CaCl_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human a-thrombin ($K_m$=125 µM) and bovine trypsin ($K_m$=125 µM). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc (Cbz-Gly-Pro-Arg-7-amino-4-trifluoromethyl coumarin) ($K_m$=27 µM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i = 1 + [I]/K_i \quad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

In Vivo Studies To Measure Thombotic Occlusions

Applicants have conducted in vivo studies of the compounds claimed herein using the following rat ferric chloride assay.

In the assay used to determine in vivo activity of the thrombin inhibitors or the invention, Male Sprague-Dawley rats (body weights 200–350 grams) were anesthetized with dial-urethane solution (0.1 ml/100 gm body weight i.p.), and a lateral tail vein was cannulated with a 23 gauge needle connected to a 12 inch length of PE50 tubing. The tubing was attached to a 3-way valve by a tubing adapter. Saline (control) or test compound, as appropriate, was administered via the tail vein catheter. A tracheostomy was performed with a 0.75 inch length of PE205 tubing. The right carotid artery was exposed and a 1.3 mm diameter Doppler flow probe was placed on the vessel. Body temperature was maintained at 37° C. using a heat lamp.

Rats (8–10/group) were randomized to continuous intravenous infusions of saline or test compound administered via the tail vein at a rate of 0.028 ml/min. Treatment infusions were initiated 60 min before the placement of a 3 mm square piece of Whatman No. 1 filter paper saturated with 35% $FeCl_3$ onto the exposed carotid artery distal to the flow probe. Treatment infusions were continued for an additional 90 minutes after the application of $FeCl_3$ (total infusion duration 150 minutes) if thrombotic occlusions did not occur, or were terminated 30 minutes after thrombotic occlusion of the vessel. Time to occlusion was defined as the time from application of $FeCl_3$ to thrombotic occlusion of the vessel. At the termination of the study (90 minutes after application of $FeCl_3$ in animals which did not occlude, or at 30 minutes after thrombotic occlusion), 3 ml blood samples were drawn by cardiac puncture into 0.3 ml of 3.8% sodium citrate.

The results show that compounds of the invention prevent thrombotic occulsions.

Thrombin Inhibitors—Therapeutic Uses

Anticoagulant therapy is indicated for the treatment and prevention of a variety of thrombotic conditions, particularly coronary artery and cerebrovascular disease. Those experienced in this field are readily aware of the circumstances requiting anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be combined with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be combined to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.1 mg per kg of body weight per day (mg/kg/day) to about 100 mg/kg/day and preferably 1.0–100 mg/kg/day and most preferably 1–20 mg/kg/day. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

For example, oral tablets can be prepared which contain an amount of active compound of between 100 and 500 mg, typically between 200 and 250 mg. Typically, a patient in need of thrombin inhibitor compound, depending on weight and metabolism of the patient, would be administered between about 100 and 1000 mg active compound per day. For a patient requiring 1000 mg per day, two tablets containing 250 mg of active compound can be administered in the morning and two tablets containing 250 mg of active compound can again be administered in the evening. For a patient requiting 500 mg per day, one tablet containing 250 mg of active compound can be administered in the morning and one tablet containing 250 mg of active compound can again be administered in the evening.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, nontoxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-coagulation agents or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

What is claimed is:

1. A compound having the formula:

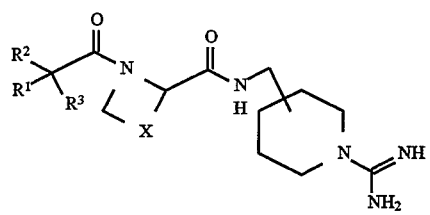

wherein

R$^1$ and R$^2$ are independently
hydrogen,
phenyl unsubstituted, mono- or di-substituted with OH, C$_{1-4}$ alkyl, oxo, or halo,
naphthyl,
biphenyl,
a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S, C$_{1-4}$ alkyl, branched $C_{1-4}$ alkyl,
$C_{3-7}$ cycloalkyl,
$C_{5-12}$ bicyclic alkyl,
$C_{11-16}$ tricyclic alkyl,
$R^4(CH_2)_n$,
$(R^4)_2CH$, wherein $R^4$ is the same or different,
$(R^4)(R^4O)CH$, wherein $R^4$ is the same or different,
$R^4O(CH_2)_n$, or
$R^2$ may be joined with $R^1$ to form a four- to seven membered carbon ring in which zero to two carbon atoms may be substituted with heteroatoms independently selected from the list N, O, and S, where n is 1, 2, 3 or 4; and
$R^3$ is
H,
$HO(CH_2)_p$, where p is 0, 1, 2, 3 or 4;
or

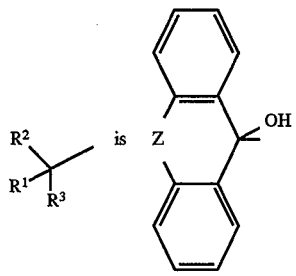

wherein Z is C, O or a bond;
provided that when $R^3$ is hydrogen and either one of $R^1$ or $R^2$ is hydrogen, the other of $R^1$ and $R^2$ is not
phenyl,
mono-hydroxy substituted phenyl
a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N,O and S.
$C_{3-7}$ cycloalkyl,
$C_{5-12}$ bicyclic heterocyclic, or
$R^4(CH_2)_n$, where n is 1, 2, 3, or 4, and $R^4$ is
phenyl,
mono-hydroxy substituted phenyl,
a 5-to 7-membered mono or bicyclic heterocyclic ring or bicyclic heterocyclic ring system any ring of which may he saturated or unsaturated, and which consists of carbon atoms and from one to three heteroatoms selected from the group consisting of N, O and S,
$C_{3-7}$ cycloalkyl, or
$C_{5-12}$ bicyclic alkyl;
$R^4$ is
phenyl unsubstituted, mono- or di-substituted with OH, OMe, $C_{1-4}$ alkyl, oxo, or halo,
naphthyl,
biphenyl,
1-dibenzocycloheptene,
a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
$C_{1-4}$ alkyl, branched $C_{1-4}$ alkyl,
$C_{3-7}$ cycloalkyl,
$C_{5-12}$ bicyclic alkyl, or
$C_{11-16}$ tricyclic alkyl; and, X is
$(CH_2)q$ where q is 1 or 2,
$NR^1CH_2$, or
$SCH_2$, or a pharmaceutically acceptable salt thereof.

2. A compound of claim 1 having the structure

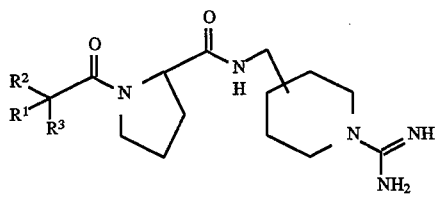

wherein
$R^1$ and $R^2$ are independently
hydrogen,
phenyl unsubstituted, mono- or di-substituted with OH, $C_{1-4}$ alkyl, oxo, or halo,
naphthyl,
biphenyl,
a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
$C_{1-4}$ alkyl,
branched $C_{1-4}$ alkyl,
$C_{3-7}$ cycloalkyl,
$C_{5-12}$ bicyclic alkyl,
$C_{11-16}$ tricyclic alkyl,
$R^4(CH_2)_n$,
$(R^4)_2CH$, wherein $R^4$ is the same or different,
$(R^4)(R^4O)CH$, wherein $R^4$ is the same or different,
$R^4O(CH_2)_n$, or
$R^2$ may be joined with $R^1$ to form a four- to seven membered carbon ring in which zero to two carbon atoms may be substituted with heteroatoms independently selected from the list N, O, and S, where n is 1, 2, 3 or 4; and
$R^3$ is
H,
$HO(CH_2)_p$, where p is 0, 1, 2, 3 or 4;
or

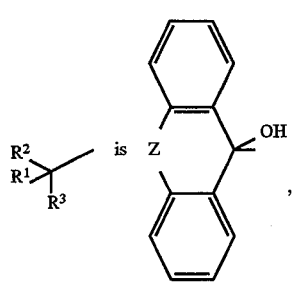

wherein Z is C, O or a bond;
provided that when $R^3$ is hydrogen and either one of $R^1$ or $R^2$ is hydrogen, the other of $R^1$ and $R^2$ is not phenyl,
mono-hydroxy substituted phenyl,
a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
$C_{3-7}$ cycloalkyl,
$C_{5-12}$ bicyclic alkyl, or
$R^4(CH_2)_n$, where n is 1, 2, 3, or 4, and $R^4$ is
phenyl,
mono-hydroxy substituted phenyl,
a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O an S,
$C_{3-7}$ cycloalkyl, or
$C_{5-12}$ bicyclic alkyl;

$R^4$ is
phenyl unsubstituted, mono- or di-substituted with OH, OMe, $C_{1-4}$ alkyl, oxo, or halo,
naphthyl,
biphenyl,
1-dibenzocycloheptene,
a 5-to 7-membered mono- or bicyclic heterocyclic ring or bicyclic heterocyclic ring system any ring of which may be saturated or unsaturated, and which consists of carbon atoms and from one to three heteroatoms selected from the group consisting of N, O and S,
$C_{1-4}$ alkyl,
branched $C_{1-4}$ alkyl,
$C_{3-7}$ cycloalkyl,
$C_{5-12}$ bicyclic alkyl, or
$C_{11-16}$ tricyclic alkyl,
or a pharmaceutically acceptable salt thereof.

3. A compound of claim 2 having the formula wherein
$R^1$ and $R^2$ are independently
hydrogen,
phenyl unsubstituted, mono- or di-substituted with OH, $C_{1-4}$ alkyl, oxo, or halo,
$(R^4)_2CH$, wherein $R^4$ is the same or different,
$R^2$ may be joined with $R^1$ to form a four- to seven membered carbon ring in which zero to two carbon atoms may be substituted with heteroatoms independently selected from the list N, O, and S,
where n is 1, 2, 3 or 4; and
$R^3$ is
H,
$HO(CH_2)_p$, where p is 0, 1, 2, 3 or 4;
or $R^2\underset{R^3}{\overset{R^1}{-}}$ is Z wherein Z is C, O or a bond;

provided that when $R^3$ is hydrogen and either one of $R^1$ or $R^2$ is hydrogen, the other of $R^1$ and $R^2$ is not phenyl or mono-hydroxy substituted phenyl, $R^4$ is
phenyl unsubstituted, mono- or di-substituted with OH, OMe, $C_{1-4}$ alkyl, oxo, or halo,
1-dibenzocycloheptene,
a 6-membered monocyclic heterocyclic ring which may be saturated or unsaturated, and which consists of carbon atoms and from one to three N heteroatoms, or
$C_{3-7}$ cycloalkyl,
or a pharmaceutically acceptable salt thereof.

4. A compound of claim 3 selected from the group consisting of

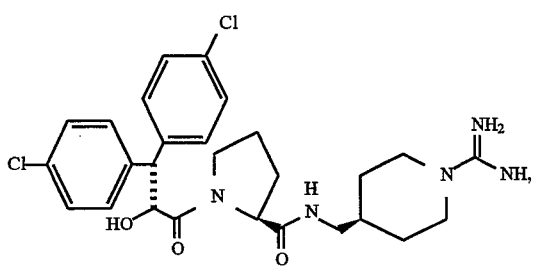

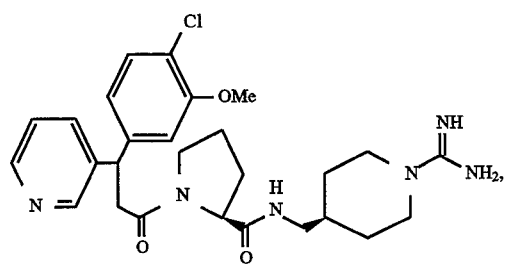

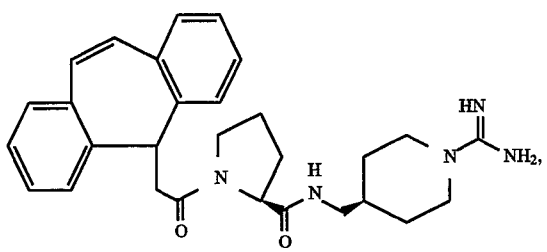

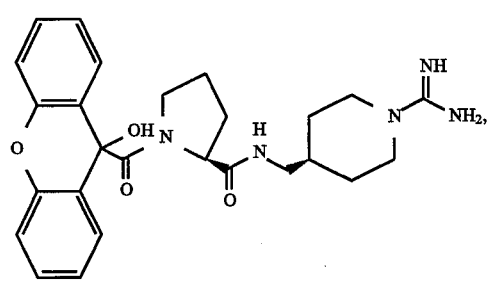

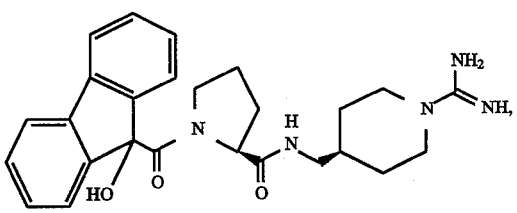

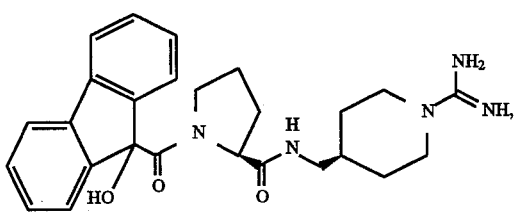

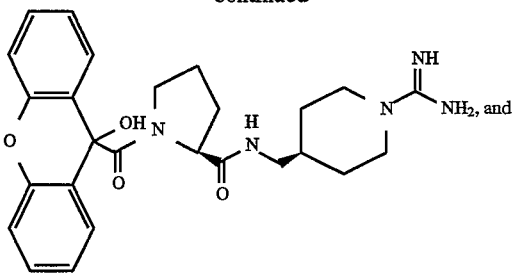

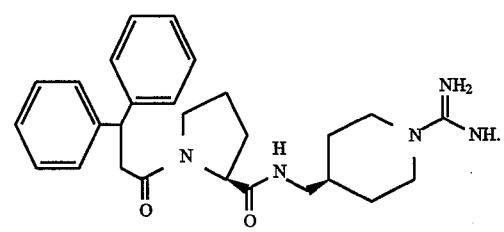

and pharmaceutically acceptable salts thereof.

5. A compound of claim 1 which is

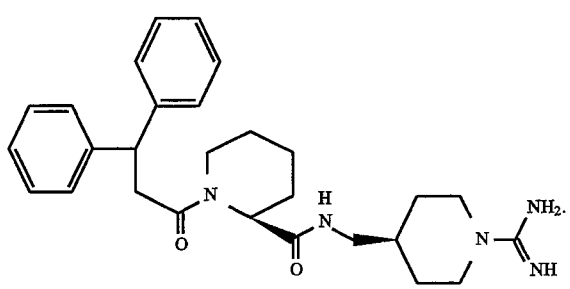

6. A composition for inhibiting thrombin in blood comprising a thrombin inhibitory effective amount of a compound of claim 1 and a pharmaceutically acceptable carrier.

7. A method for inhibiting thrombin in blood in a mammal comprising administering to the mammal an anti-thrombin effective amount of a composition of claim 6.

8. A method for inhibiting formation of blood platelet aggregates in blood in a mammal comprising administering to the mammal an anti-thrombin effective amount of a composition claim 6.

9. A method for inhibiting thrombus formation in blood in a mammal comprising administering to the mammal an anti-thrombin effective a composition claim 6.

* * * * *

UNITED STATES PATENT AND TRADEMARK OFFICE
CERTIFICATE OF CORRECTION

PATENT NO. : 5,629,324

DATED : 5/13/97

INVENTOR(S) : Joseph P. Vacca, William C. Lumma, Stephen F. Brady, and Thomas J. Tucker It is certified that error appears in the above-identified patent and that said Letters Patent is hereby corrected as shown below:

In Column 17, line 43, change "heterocyclic" to -- alkyl --.

Signed and Sealed this

Ninth Day of September, 1997

Attest:

BRUCE LEHMAN

*Attesting Officer*    *Commissioner of Patents and Trademarks*